(12) United States Patent
Kogure

(10) Patent No.: US 9,636,006 B2
(45) Date of Patent: May 2, 2017

(54) ENDOSCOPE CLEANING/DISINFECTING APPARATUS

(71) Applicant: OLYMPUS CORPORATION, Tokyo (JP)

(72) Inventor: Hisato Kogure, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/952,273

(22) Filed: Nov. 25, 2015

(65) Prior Publication Data

US 2016/0074912 A1 Mar. 17, 2016

Related U.S. Application Data

(63) Continuation of application No. PCT/JP2014/076308, filed on Oct. 1, 2014.

(30) Foreign Application Priority Data

Feb. 19, 2014 (JP) ................................. 2014-029891

(51) Int. Cl.
*A61B 1/12* (2006.01)
*A61B 90/70* (2016.01)
(Continued)

(52) U.S. Cl.
CPC .............. *A61B 1/123* (2013.01); *A61B 90/70* (2016.02); *B08B 3/08* (2013.01); *A47L 15/4259* (2013.01);
(Continued)

(58) Field of Classification Search
CPC .... A61B 1/123; A61B 90/70; A61B 2090/701
See application file for complete search history.

(56) References Cited

U.S. PATENT DOCUMENTS

| 2009/0065034 A1* | 3/2009 | Suzuki | A61B 1/123 |
| | | | 134/56 R |
| 2012/0015671 A1* | 1/2012 | Lada | G06F 1/1616 |
| | | | 455/456.1 |

FOREIGN PATENT DOCUMENTS

| CN | 101166457 B | 4/2010 |
| CN | 102473020 A | 5/2012 |

(Continued)

OTHER PUBLICATIONS

Machine Translation of JP2013-106790A, dated Jun. 6, 2013.*
(Continued)

*Primary Examiner* — Spencer Bell
(74) *Attorney, Agent, or Firm* — Scully, Scott, Murphy & Presser, P.C.

(57) ABSTRACT

An endoscope cleaning/disinfecting apparatus includes: a cleaning/disinfecting tank; a cover portion; a facing portion; an approach portion; a central portion; an acceleration sensor detecting an acceleration change pattern at time of the cover portion moving from an open position to a closed position; an informing section; and a control section, when the acceleration change pattern detected by the acceleration sensor is different from a set pattern at the time of the cover portion moving from the open position to the closed position, judging that the approach portion comes into contact with the cleaning/disinfecting target and performing warning control of the informing section. A shortest distance between the approach portion and the cleaning/disinfecting tank at time of the approach portion being fitted into a hollow portion at the closed position is less than 3.2 mm.

8 Claims, 9 Drawing Sheets

(51) Int. Cl.
  *B08B 3/08*   (2006.01)
  *A47L 15/42*  (2006.01)
  *D06F 37/42*  (2006.01)
  *D06F 39/14*  (2006.01)

(52) U.S. Cl.
  CPC ........ *A61B 2090/701* (2016.02); *D06F 37/42* (2013.01); *D06F 39/14* (2013.01); *D06F 2224/00* (2013.01)

(56) References Cited

FOREIGN PATENT DOCUMENTS

| | | |
|---|---|---|
| EP | 2 599 424 A1 | 6/2013 |
| JP | 2002-272822 A | 9/2002 |
| JP | 2006-230491 A | 9/2006 |
| JP | 2010-57792 A | 3/2010 |
| JP | 2010-284213 A | 12/2010 |
| JP | 2013-103017 A | 5/2013 |
| JP | 2013-106790 A | 6/2013 |

OTHER PUBLICATIONS

International Search Report dated Jan. 13, 2015 issued in PCT/JP2014/076308.
Japanese Office Action dated Jun. 3, 2015 issued in JP 2015-512957.
Extended Supplementary European Search Report dated Jan. 16, 2017 in European Patent Application No. 14 88 3214.0.

\* cited by examiner

ENDOSCOPE CLEANING/DISINFECTING APPARATUS

CROSS REFERENCE TO RELATED APPLICATION

This application is a continuation application of PCT/JP2014/076308 filed on Oct. 1, 2014 and claims benefit of Japanese Application No. 2014-029891 filed in Japan on Feb. 19, 2014, the entire contents of which are incorporated herein by this reference.

BACKGROUND OF THE INVENTION

1. Field of the Invention

The present invention relates to an endoscope cleaning/disinfecting apparatus having a cover portion which is automatically opened and closed freely.

2. Description of the Related Art

When cleaning and disinfecting a cleaning/disinfecting target object, for example, an endoscope using an endoscope cleaning/disinfecting apparatus, an operator first arranges the used endoscope on a bottom surface of a hollow portion of a cleaning/disinfecting tank and connects various tubes to a cap of the endoscope. After that, the operator closes a cover portion and presses a start button.

After that, a cleaning/disinfecting process starts, and the cleaning/disinfecting process ends after a predetermined time period elapses. Lastly, the operator opens the cover portion and takes out the cleaned and disinfected endoscope.

Japanese Patent Application Laid-Open Publication No. 2010-284213 discloses a cleaning/disinfecting apparatus having an automatic opening/closing mechanism for automatically opening and closing a cover portion.

Further, Japanese Patent Application Laid-Open Publication No. 2010-284213 discloses a configuration in which a position sensor for detecting an opening/closing position is provided on a hinge portion for opening and closing a cover portion.

By the way, the cover portion is provided with a watertight member for, when the cover portion is closed, keeping the cleaning/disinfecting tank watertight by being pressed to an approach portion provided on a perimeter of the hollow portion of the cleaning/disinfecting tank and adhering to the approach portion, being deformed.

Here, as disclosed in Japanese Patent Application Laid-Open Publication No. 2010-284213, if an insertion portion has a large diameter in a case where, in the configuration in which the cover portion is automatically opened and closed, a part of the insertion portion of an endoscope arranged in the hollow portion of the cleaning/disinfecting tank protrudes outside the cleaning/disinfecting tank, it does not happen that the cover portion is closed even if the watertight member is compressed when the insertion portion with the large diameter is sandwiched between the approach portion and the watertight member, because the insertion portion gets in the way because it has a large diameter. That is, it does not happen that a closed position sensor detects the closed position of the cover portion.

SUMMARY OF THE INVENTION

An endoscope cleaning/disinfecting apparatus in an aspect of the present invention is provided with: a cleaning/disinfecting tank having a hollow portion, a perimeter fringe portion surrounding a perimeter of the hollow portion, and an arrangement portion where a cleaning/disinfecting target object is arranged, on a bottom surface of the hollow portion; a cover portion being automatically opened and closed freely relative to an opening of the cleaning/disinfecting tank; a facing portion provided on the cover portion and facing the perimeter fringe portion at a closed position where the cover portion covers the opening; an approach portion provided on an inner side with respect to the facing portion on the cover portion, the approach portion being fitted in the hollow portion at the closed position and freely coming into contact with the cleaning/disinfecting target object; a central portion provided on an inner side with respect to the approach portion on the cover portion and covering the arrangement portion at the closed position; an acceleration sensor detecting an acceleration change pattern when the cover portion moves from an open position to the closed position; an informing section giving a warning; and a control section performing automatic opening/closing control of the cover portion, and, when the acceleration change pattern detected by the acceleration sensor is different from a set pattern at the time of the cover portion moving from the open position to the closed position, judging that the approach portion comes into contact with the cleaning/disinfecting target object and performing warning control of the informing section, wherein a shortest distance between the approach portion and the cleaning/disinfecting tank at the time of the approach portion being fitted into the hollow portion at the closed position is less than 3.2 mm.

DETAILED DESCRIPTION OF THE PREFERRED EMBODIMENTS

Embodiments of the present invention will be described below with reference to drawings. Note that, since the drawings are schematic, a relationship between thickness and width of each member, a ratio of thicknesses of respective members and the like are different from actual ones. Of course, among the drawings, parts having a different dimensional relationship and ratio are included.

First Embodiment

Figure 1:
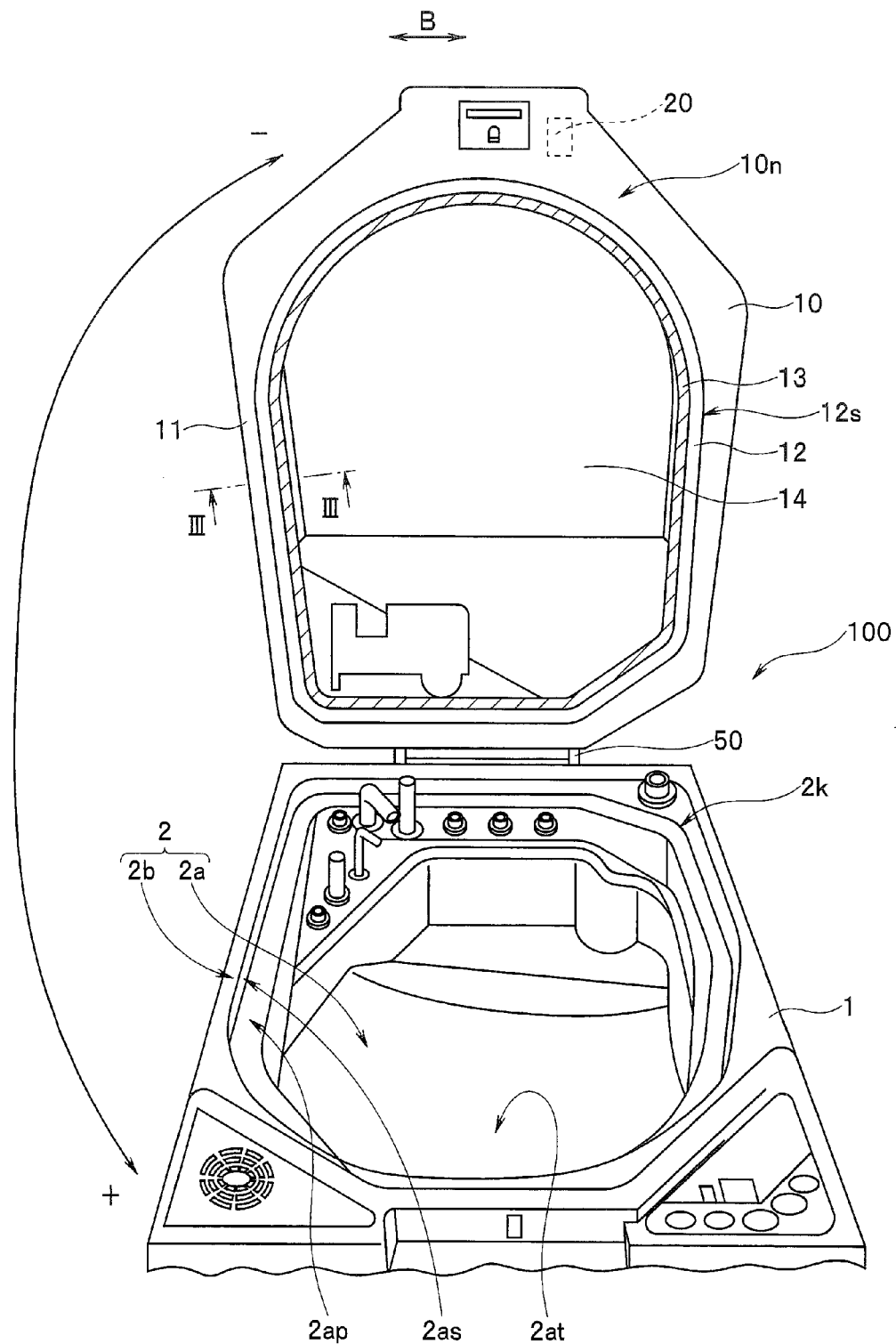
FIG. 1 is a partial perspective view showing an endoscope cleaning/disinfecting apparatus of a first embodiment in a state that a cover portion is open relative to an apparatus body.
Figure 2:
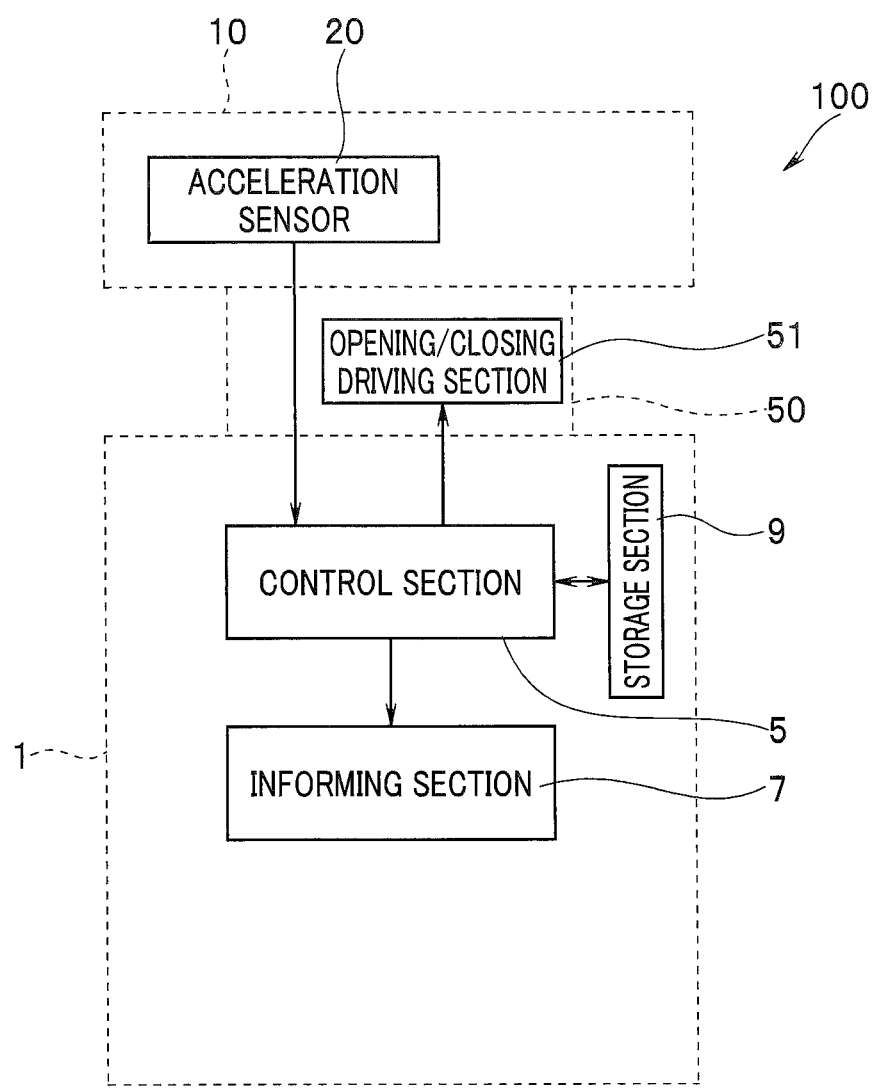
FIG. 2 is a block diagram schematically showing a configuration for automatically opening and closing the cover portion of FIG. 1.
Figure 3:
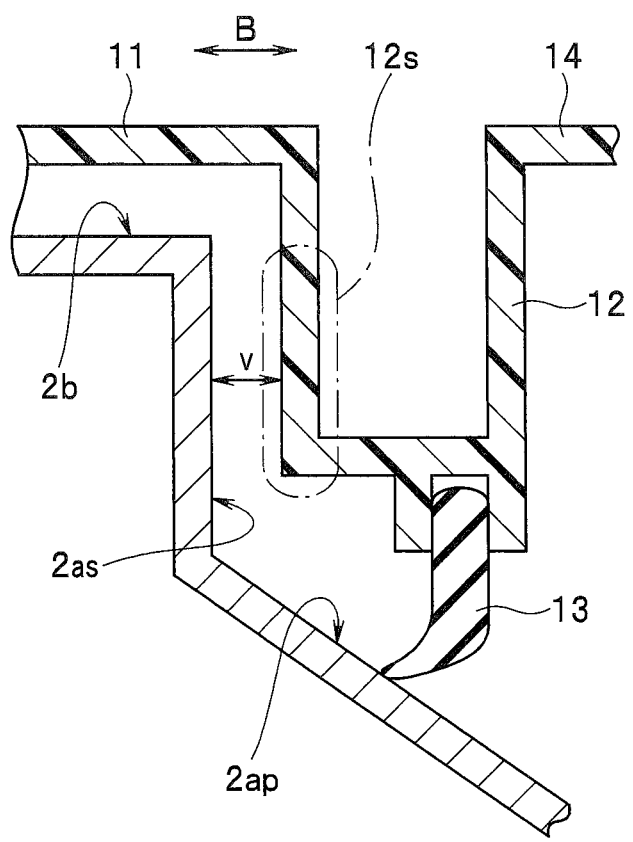
FIG. 3 is a partial cross-sectional view along a III-III line in FIG. 1 in a state that the cover portion of FIG. 1 is closed at a closed position.

FIG. 1 is a partial perspective view showing an endoscope cleaning/disinfecting apparatus of a first embodiment in a state that a cover portion is open relative to an apparatus body; FIG. 2 is a block diagram schematically showing a configuration for automatically opening and closing the cover portion of FIG. 1; FIG. 3 is a partial cross-sectional view along a line in FIG. 1 in a state that the cover portion of FIG. 1 is closed at a closed position; and FIG. 4 is a partial cross-sectional view showing a state that an approach portion of the cover portion of FIG. 3 is in contact with an insertion portion of an endoscope.

Figure 4:
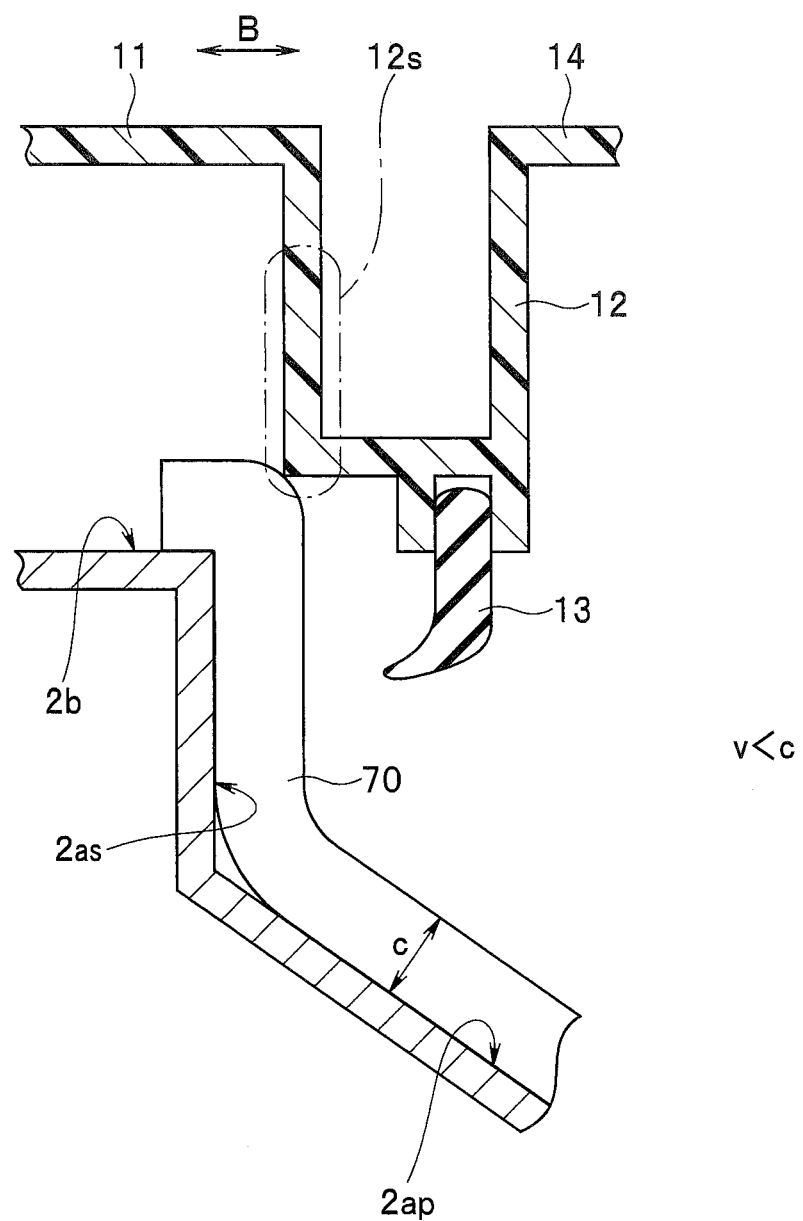
FIG. 4 is a partial cross-sectional view showing a state that an approach portion of the cover portion of FIG. 3 is in contact with an insertion portion of an endoscope.
Figure 5:
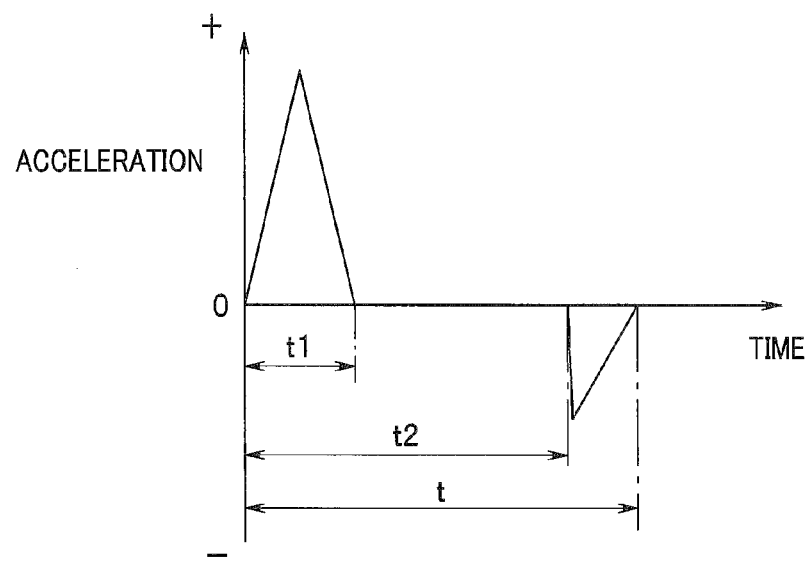
FIG. 5 is a chart showing a set pattern for an acceleration change pattern of the cover portion of FIG. 1 when the cover portion moves from an open position to the closed position in a predetermined, time period.
Figure 6:
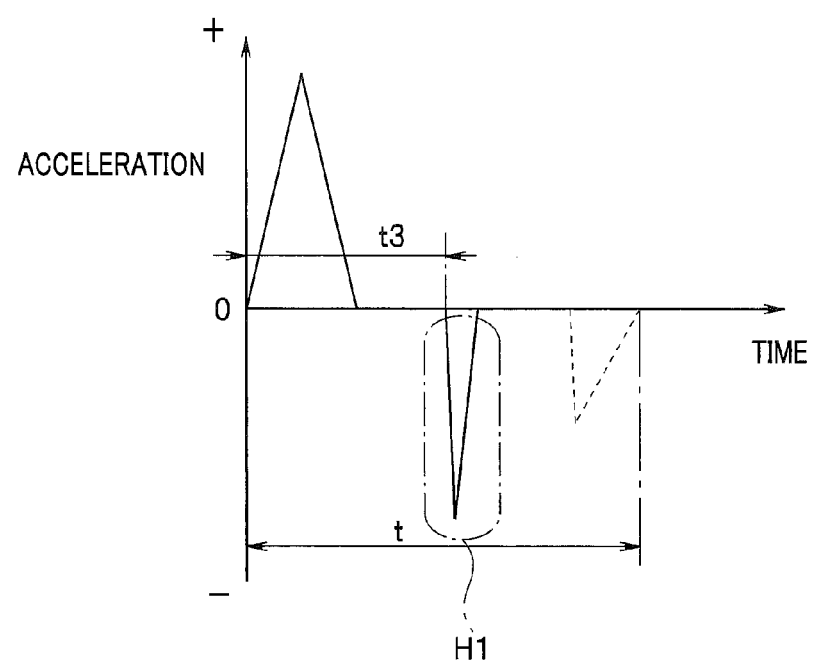
FIG. 6 is a chart showing an acceleration change pattern of the cover portion in a case where the approach portion of the cover portion of FIG. 4 is in contact with the insertion portion of the endoscope.

Further, FIG. 5 is a chart showing a set pattern for an acceleration change pattern of the cover portion of FIG. 1 when the cover portion moves from an open position to the closed position in a predetermined time period; and FIG. 6 is a chart showing an acceleration change pattern of the cover portion in a case where the approach portion of the cover portion of FIG. 4 is in contact with the insertion portion of the endoscope.

As shown in FIG. 1, an endoscope cleaning/disinfecting apparatus 100 is provided with an apparatus body 1, and a cover portion 10 connected in a state of being freely opened and closed, for example, via a hinge 50 at an upper part of the apparatus body 1.

Further, a cleaning/disinfecting tank 2 which accommodates a cleaning/disinfecting target object to be cleaned and disinfected with use of the endoscope cleaning/disinfecting apparatus 100 is provided at an upper part of the apparatus body 1. Note that, in the present embodiment, description will be made on an endoscope as an example of the cleaning/disinfecting target object.

A main part of the cleaning/disinfecting tank 2 is configured being provided with a hollow portion 2a and a perimeter fringe portion 2b surrounding a perimeter of the hollow portion 2a.

An arrangement portion 2at where an endoscope is to be arranged is configured on a bottom surface of the hollow portion 2a. Further, the hollow portion 2a is connected to the perimeter fringe portion 2b via a circular-shaped side wall 2as and has a circular-shaped abutting portion 2ap to which a watertight member 13 to be described later closely adheres when the cover portion 10 is closed. Note that the abutting portion 2ap may be formed on an inclined plane as shown in FIG. 3 or on a flat plane.

The cover portion 10 is automatically opened and closed freely relative to an opening 2k of the cleaning/disinfecting tank 2 by automatic opening/closing control by a control section 5 (see FIG. 2).

More specifically, as shown in FIG. 2, the cover portion 10 is automatically opened and closed freely in a predetermined time period t (see FIG. 5) relative to the opening 2k, for example, by the control section 5 provided in the apparatus body 1 performing drive control of an opening/closing driving section 51 provided on the hinge 50.

Note that the opening/closing driving section 51 may be provided in the apparatus body 1 or the cover portion 10. Further, as the opening/closing driving section 51, for example, a motor can be given.

Therefore, if the opening/closing driving section 51 is configured with a motor, the control section 5 only has to control motor speed in order to perform automatic opening/closing control of the cover portion 10 in the predetermined time t. As what the opening/closing driving section 51 is configured with, a cylinder driven by utilizing an electromagnet or pressure of fluid can be given in addition to a motor.

Returning to FIG. 1, the cover portion 10 is provided with: a facing portion 11 which faces the perimeter fringe portion 2b at the closed position shown in FIG. 3 where the cover portion 10 covers the opening 2k, a projecting portion 12 which is provided on an inner side with respect to the facing portion 11 in a width direction B of the endoscope cleaning/disinfecting apparatus 100, and a central portion 14 which is provided on an inner side with respect to the projecting portion 12 in the width direction B and which covers the arrangement portion 2at at the closed position.

More specifically, the facing portion 11, the projecting portion 12 and the central portion 14 are provided on an internal surface 10n of the cover portion 10 which faces the opening 2k at the closed position.

Note that the cover portion 10 is locked to the apparatus body 1 by a latch or the like not shown at the closed position.

As shown in FIG. 3, the projecting portion 12 is a region which projects into the hollow portion 2a at the closed position of the cover portion 10, and an approach portion 12s is provided at a position surrounded by a dashed-dotted line in FIG. 3 on the projecting portion 12, which faces the side wall 2as at the closed position.

Further, the watertight member 13, which is pressed to and closely adheres to the cleaning/disinfecting tank 2, for example, the abutting portion 2ap of the hollow portion 2a, being deformed, at the closed position of the cover portion 10 is provided on an inner side with respect to the approach portion 12s on a projecting surface of the projecting portion 12 in the width direction B.

The watertight member 13 is a member for preventing liquid from leaking to an outside of the cleaning/disinfecting tank 2 during a cleaning/disinfecting process of the endoscope cleaning/disinfecting apparatus 100, and is configured with an elastic member, for example, a packing.

The approach portion 12s is provided at a position on the internal surface 10n of the cover portion 10 where, when the approach portion 12s is fitted into the hollow portion 2a at the closed position of the cover portion 10, a distance v to the cleaning/disinfecting tank 2, for example, the side wall 2as of the hollow portion 2a is less than a diameter c of an insertion portion 70 (v<c) because of a reason to be described later. More specifically, the approach portion 12s is provided at a position on the internal surface 10n of the cover portion 10 where the distance v is less than 2.5 mm, that is, equal to or more than 0 mm and less than 2.5 mm.

Further, as shown in FIG. 4, the approach portion 12s is adapted to be able to, when a part of the insertion portion 70 of the endoscope arranged on the arrangement portion 2at protrudes to the perimeter fringe portion 2b, come into contact with the insertion portion 70 before the cover portion 10 moves to the closed position where the watertight member 13 closely adheres to the abutting portion 2ap, irrespective of the diameter of the insertion portion 70.

More specifically, the approach portion 12s is adapted to be able to come into contact with the insertion portion 70 which protrudes to an outer side with respect to the watertight member 13 in the width direction B.

Note that the reason why the distance v is set less than 3.2 mm is that, since there are some endoscopes with a diameter c of 3.2 mm among endoscopes categorized as small-diameter ones at present, it is possible to, if the distance v is set less than 3.2 mm, certainly cause the approach portion 12s to come into contact with the insertion portion 70 as shown in FIG. 4 when the cover portion 10 is closed in the case where the insertion portion 70 protrudes on the perimeter fringe portion 2b.

Further, since endoscopes with a diameter c of 2.5 mm also exist, the distance v is preferably less than 2.5 mm. A lower limit of the distance v is 0 mm.

Further, as shown in FIGS. 1 and 2, the cover portion 10 is provided with an acceleration sensor 20 which detects an acceleration change pattern when the cover portion 10 moves from the open position shown in FIG. 1 to the closed position shown in FIG. 3 where the watertight member 13 closely adheres to the abutting portion 2ap.

Note that a set pattern for acceleration change when the cover portion 10 normally moves from the open position to the closed position shown in FIG. 5 is stored in a storage section 9 provided in the apparatus body 1 as shown in FIG. 2. Note that a place to arrange the storage section 9 is not especially limited and may be provided, for example, in the cover portion 10.

Further, as shown in FIG. 5, the set pattern for the acceleration change pattern shows that, when the cover portion 10 begins to be closed from the open position, speed accelerates in a + (plus) direction in the predetermined time period t. After that, the acceleration becomes 0 at time t1. When the watertight member 13 begins to be in contact with the abutting portion 2ap at time t2, the speed begins to accelerate in a − (minus) direction. When the watertight member 13 is deformed and closely adheres at the closed position, the speed accelerates in the + (plus) direction and, lastly, becomes 0 in the predetermined time period t.

Note that, hereinbelow, the acceleration in the direction of the cover portion 10 moving from the open position to the closed position is defined as + (plus), and the acceleration in the direction of moving from the closed position to the open position is defined as − (minus).

Further, a place to provide the acceleration sensor 20 is not limited to the cover portion 10. The acceleration sensor 20 may be provided in a member moving between the open position and the closed position together with the cover portion 10, for example, the hinge 50.

If the acceleration change pattern detected by the acceleration sensor 20 is different from the set pattern stored in the storage section 9, which is shown in FIG. 5, the control section 5 judges that the approach portion 12s has come into contact with the insertion portion 70 and performs warning control of an informing section 7 which is provided in the apparatus body 1 and gives a warning. Thereby, an operator is caused to recognize that the insertion portion 70 is sandwiched between the cleaning/disinfecting tank 2 and the cover portion 10 at the closed position of the cover portion 10.

More specifically, as shown in FIG. 6, if the approach portion 12s comes into contact with the insertion portion 70 as shown in FIG. 4 at time t3 before the time t2 when the control section 5 performs drive control of the opening/closing driving section 51 to move the cover portion 10 from the open position to the closed position in the predetermined time period t, the acceleration sensor 20 detects sudden acceleration change in the − (minus) direction as indicated by a surrounding dashed-dotted line H1.

By detecting the sudden change from the acceleration sensor 20, the control section 5 judges that the acceleration change pattern is different from the set pattern shown in FIG. 5 and performs warning control using the informing section 7.

Note that, in a case of a small-diameter insertion portion of an endoscope, if the insertion portion is sandwiched, for example, between the abutting portion 2ap and the watertight member 13 acceleration change is difficult to occur because the watertight member 13 is compressed and absorbs an impact of being sandwiched; and there is a possibility that, though the cover portion 10 is closed in the state that the insertion portion remains being sandwiched, the acceleration sensor 20 detects an acceleration change pattern corresponding to the set pattern shown in FIG. 5.

Therefore, in the present embodiment, by setting the distance v described above less than 3.2 mm, preferably 2.5 mm, the approach portion 12s certainly comes into contact with the insertion portion before the watertight member 13 closely adheres to the abutting portion 2ap if the cover portion 10 is closed so that sudden acceleration change accompanying the contact can be detected by the acceleration sensor 20 and, thereby, it can be detected that the insertion portion is sandwiched.

Note that, when judging that the approach portion 12s has come into contact with the insertion portion 70, the control section 5 may perform automatic control to open the cover portion 10 onto the open position side in order to prevent breakage of the insertion portion 70.

Note that the automatic control in this case may be control to open the cover portion 10 completely to the open position or may be control to open the cover portion 10 not completely but only a little, that is, onto the open position side by a predetermined amount.

As described above, in the present embodiment, it is shown that the insertion portion 70 is arranged in the hollow portion 2a of the cleaning/disinfecting tank 2, and that the approach portion 12s which, when the cover portion 10 is closed in the case where a part of the insertion portion 70 protrudes outside the cleaning/disinfecting tank, comes into contact with the insertion portion 70 before the watertight member 3 closely adheres to the abutting portion 2ap is provided on the internal surface 10n of the cover portion 10.

Further, it is shown that the distance v between the approach portion 12s and the side wall 2as of the hollow portion 2a when the cover portion 10 is closed is set less than 3.2 mm, preferably less than 2.5 mm.

From this, the approach portion 12s certainly comes into contact with the insertion portion 70 when the cover portion 10 is closed from the open position to the closed position.

Furthermore, it is shown that the cover portion 10 is provided with the acceleration sensor 20 which detects an acceleration change pattern when the cover portion 10 moves from the open position to the closed position.

Further, it is shown that, if the acceleration change pattern detected by the acceleration sensor 20 is different from the set pattern shown in FIG. 5, the control section 5 judges that the approach portion 12s has come into contact with the insertion portion 70 and performs warning control.

From this, it is possible to certainly detect that the approach portion 12s has come into contact with the insertion portion 70, that is, the insertion portion 70 was sandwiched between the cleaning/disinfecting tank 2 and the cover portion 10 when the cover portion 10 was closed, and it is also possible to give a warning to the operator.

Therefore, in addition to being able to prevent it from happening that the insertion portion 70 is sandwiched between the cleaning/disinfecting tank 2 and the cover portion 10 and is broken, it is also possible to prevent it from happening that the cleaning/disinfecting process is started while the insertion portion 70 remains protruding outside the cleaning/disinfecting tank 2, and liquid scatters outside the endoscope cleaning/disinfecting apparatus 100 via an endoscope conduit in the insertion portion 70.

Note that, the same as above goes for a case of a cleaning/disinfecting target object other than the insertion portion 70 of an endoscope.

From the above, it is possible to provide an endoscope cleaning/disinfecting apparatus provided with a configuration capable of certainly detecting that a cleaning/disinfecting target object is sandwiched between a cover portion which is automatically opened and closed and a cleaning/disinfecting tank and giving a warning to an operator.

Second Embodiment

Figure 7:
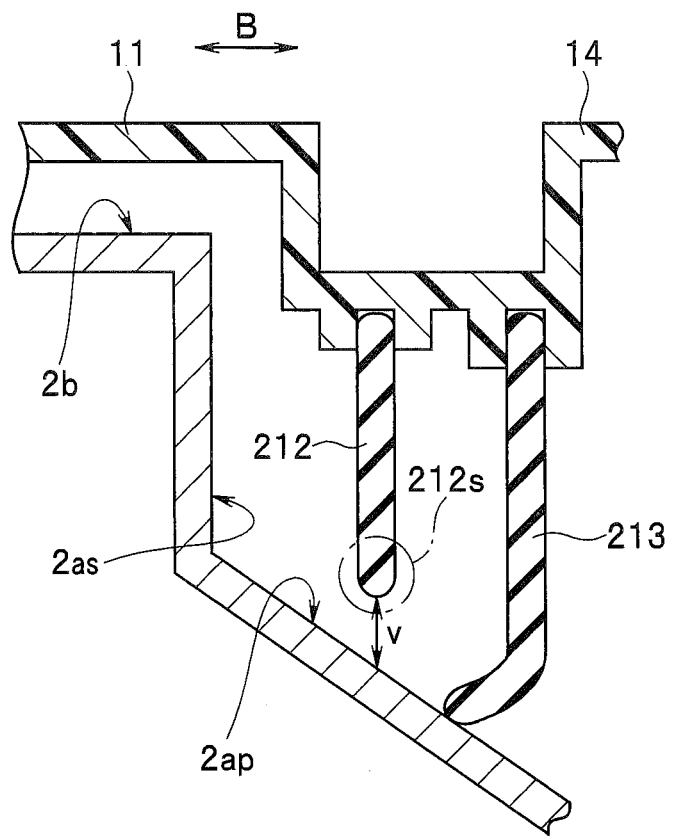
FIG. 7 is a partial cross-sectional view of a same position as FIG. 3 in a state that a cover portion of an endoscope cleaning/disinfecting apparatus of a second embodiment is closed at a closed position.
Figure 8:
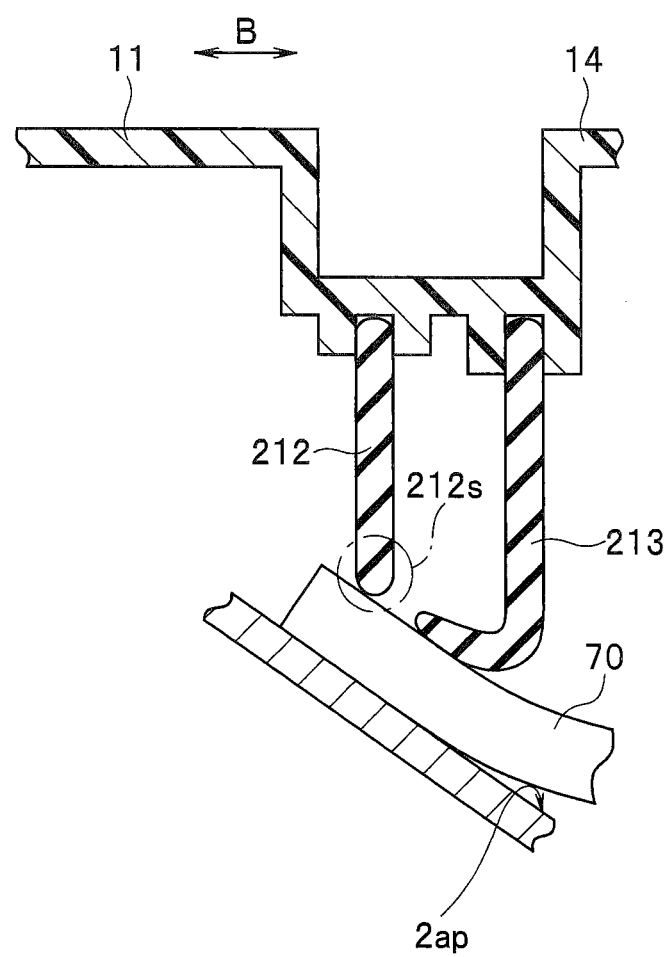
FIG. 8 is a partial cross-sectional view showing a state that an approach portion of the cover portion of FIG. 3 is in contact with an insertion portion of an endoscope.

FIG. 7 is a partial cross-sectional view of a same position as FIG. 3 in a state that a cover portion of an endoscope cleaning/disinfecting apparatus of the present embodiment is closed at a closed position; and FIG. 8 is a partial cross-sectional view showing a state that an approach portion of the cover portion of FIG. 3 is in contact with an insertion portion of an endoscope.

Figure 9:
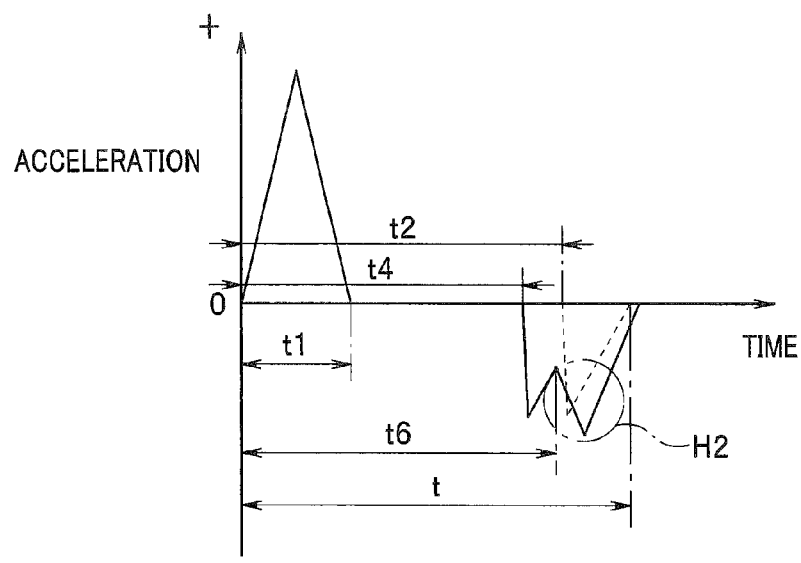
FIG. 9 is a chart showing a set pattern for an acceleration change pattern of the cover portion of FIG. 7 when the cover portion moves from an open position to the closed position in a predetermined time period together with an acceleration change pattern of the cover portion in a case where the approach portion of the cover portion comes into contact with the insertion portion of the endoscope.

FIG. 9 is a chart showing a set pattern for an acceleration change pattern of the cover portion of FIG. 7 when the cover portion moves from an open position to the closed position in a predetermined time period together with an acceleration change pattern of the cover portion in a case where the approach portion of the cover portion comes into contact with the insertion portion of the endoscope.

In comparison with the endoscope cleaning/disinfecting apparatus of the first embodiment described above, the endoscope cleaning/disinfecting apparatus of the second embodiment is different in a point that the approach portion is provided at a position facing a bottom surface of a hollow portion, on a projecting portion provided on the cover portion and projecting into the hollow portion at the closed position; and a point that the approach portion comes into contact with a cleaning/disinfecting target object after a watertight member comes into contact with the cleaning/disinfecting target object when the cover portion is closed.

Therefore, only the different points will be described. Components similar to those of the first embodiment will be given the same reference numerals, and description of the components will be omitted.

As shown in FIG. 7, in the present embodiment, a projecting portion 212 configured with an elastic material and projecting into the hollow portion 2a at the closed position of the cover portion 10 is provided on the internal surface 10n of the cover portion 10, and an approach portion 212s is provided at a position facing the arrangement portion 2at of the projecting portion 212 at the closed position, as indicated by being surrounded by a dashed-dotted line in FIG. 7.

The approach portion 212s is provided at a position on the internal surface 10n of the cover portion 10 where, when the approach portion 212s is fitted into the hollow portion 2a at the closed position of the cover portion 10, the distance v to the cleaning/disinfecting tank 2, for example, the abutting portion 2ap of the hollow portion 2a is, similarly to the first embodiment described above, less than the diameter c of the insertion portion 70 (v<c), more specifically, at a position on the internal surface 10n of the cover portion 10 where the distance v is less than 3.2 mm, preferably less than 2.5 mm.

Note that the reason why the distance v is set less than 3.2 mm, preferably less than 2.5 mm is, similarly to the first embodiment described above, to cause the approach portion 212s to be certainly in contact with the insertion portion 70 at the closed position.

Note that, in the present embodiment, if the insertion portion 70 is arranged with a part protruding outside the cleaning/disinfecting tank 2, the approach portion 212s comes into contact with the insertion portion 70 after a watertight member 213 comes into contact with the insertion portion 70 when the cover portion 10 is gradually closed, as shown in FIG. 8.

That is, the watertight member 213 is formed longer than the projecting portion 212, with the internal surface 10n of the cover portion 10 as a basis.

Note that an amount of compression of the watertight member 213 relative to the insertion portion 70 is set to such an amount that the approach portion 212s can be in contact with the insertion portion 70 when the watertight member 213 is compressed by the insertion portion 70.

If the acceleration change pattern detected by the acceleration sensor 20 is different from the set pattern stored in the storage section 9, which is shown in FIG. 9, the control section 5 judges that the approach portion 212s has come into contact with the insertion portion 70 and performs warning control of the informing section 7 which is provided in the apparatus body 1 and gives a warning. Thereby, the operator is caused to recognize that the insertion portion 70 is sandwiched between the cleaning/disinfecting tank 2 and the cover portion 10 at the closed position of the cover portion 10.

More specifically, as shown in FIG. 9, when the control section 5 performs drive control of the opening/closing driving section 51 to move the cover portion 10 from the open position to the closed position in the predetermined time period t, − (minus) acceleration occurs when the watertight member 213 comes into contact with the insertion portion 70 at time t4. However, if the approach portion 212s comes into contact with the insertion portion 70 as shown in FIG. 8 at time t6 after the time t4, the control section 5 detects an acceleration change pattern as indicated by a surrounding dashed-dotted line H2 which is different from a set pattern shown by a broken line.

By detecting the change pattern from the acceleration sensor 20, the control section 5 judges that the acceleration change pattern is different from the set pattern and performs warning control using the informing section 7.

Note that other components are the same as the first embodiment described above.

By such a configuration also, the approach portion 212s certainly comes into contact with the insertion portion 70 when the cover portion 10 is closed from the open position to the closed position.

Further, since, if the acceleration change pattern detected by the acceleration sensor 20 is different from the set pattern, the control section 5 judges that the approach portion 212s has come into contact with the insertion portion 70 and performs warning control, it is possible to certainly detect that the insertion portion 70 was sandwiched between the cleaning/disinfecting tank 2 and the cover portion 10 when the cover portion 10 was closed, and it is also possible to give a warning to the operator.

Note that other effects are the same as the first embodiment described above.

Note that a modification will be shown below with use of FIGS. 10 to 12.

Figure 10:
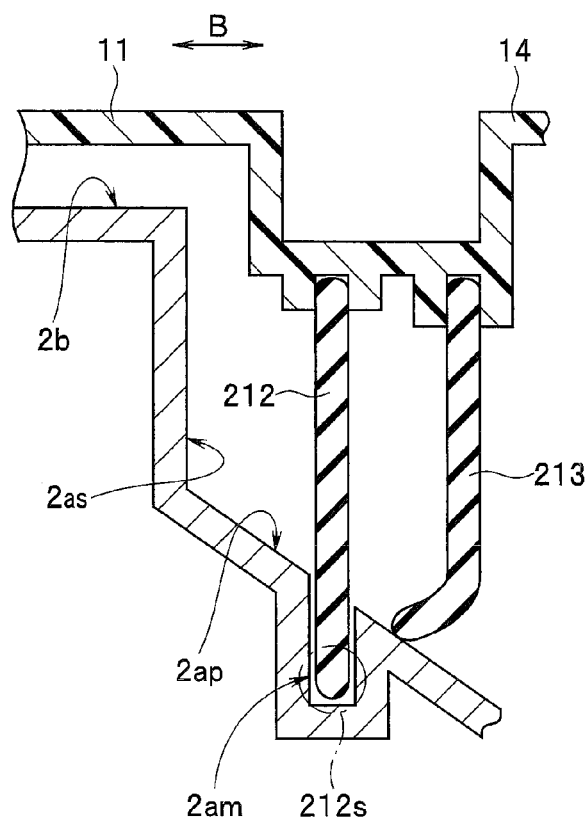
FIG. 10 is a partial cross-sectional view showing a modification in which a projecting portion is fitted in a fitting portion of a cleaning/disinfecting tank in the state that the cover portion of FIG. 7 is closed at the closed position.
Figure 11:
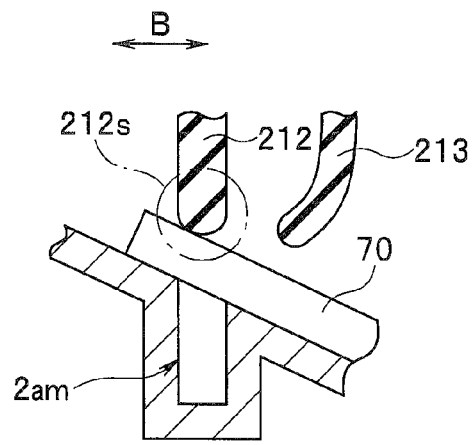
FIG. 11 is a partial cross-sectional view showing a state that the approach portion of the cover portion of FIG. 10 is in contact with the insertion portion of the endoscope.

FIG. 10 is a partial cross-sectional view showing a modification in which a projecting portion is fitted in a fitting portion of a cleaning/disinfecting tank in the state that the cover portion of FIG. 7 is closed at the closed position; and FIG. 11 is a partial cross-sectional view showing a state that the approach portion of the cover portion of FIG. 10 is in contact with the insertion portion of the endoscope.

Figure 12:
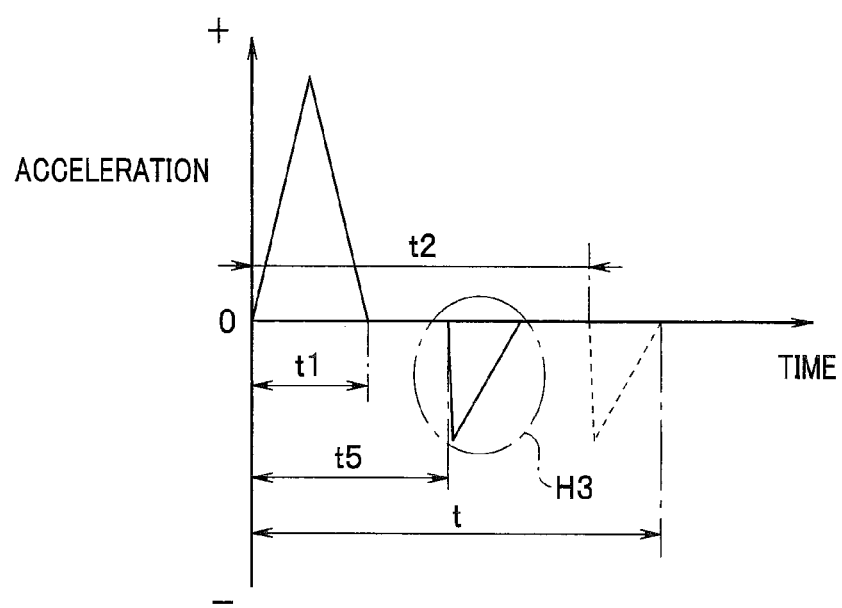
FIG. 12 is a chart showing a set pattern for an acceleration change pattern of the cover portion of FIG. 10 when the cover portion moves from an open position to the closed position in a predetermined time period together with an acceleration change pattern of the cover portion in a case where the approach portion of the cover portion comes into contact with the insertion portion of the endoscope.

FIG. 12 is a chart showing a set pattern for an acceleration change pattern of the cover portion of FIG. 10 when the cover portion moves from an open position to the closed position in a predetermined time period together with an acceleration change pattern of the cover portion in a case where the approach portion of the cover portion comes into contact with the insertion portion of the endoscope.

In the present embodiment described above, it is shown that the watertight member 213 is formed longer than the projecting portion 212, with the internal surface 10n of the cover portion 10 as a basis.

However, the configuration is not limited to this. It is also possible to foul' the projecting portion 212 with a length longer than the watertight member 213, with the internal surface 10n as a basis, which is such a length that causes the projecting portion 212 to be fitted in a fitting portion 2am, which is a groove formed on the abutting portion 2ap of the cleaning/disinfecting tank 2, at the closed position of the cover portion 10, as shown in FIG. 10.

According to such a configuration, when the cover portion 10 is closed in the case where a part of the insertion portion 70 protrudes outside the cleaning/disinfecting tank 2, an acceleration change pattern indicated by a surrounding dashed-dotted line H3 different from a set pattern shown by a broken line is detected at time t5 before the time t2 as shown in FIG. 12 if the approach portion 212s comes into contact with the insertion portion 70 before the watertight member 213 comes into contact with the insertion portion 70 as shown in FIG. 11, similarly to the first embodiment described above.

By detecting the change pattern from the acceleration sensor 20, the control section 5 judges that the acceleration change pattern is different from the set pattern and performs warning control using the informing section 7.

Note that other components are the same as of the second embodiment described above. Further, effects similar to those of the second embodiment described above can be obtained by such a configuration.

What is claimed is:

1. An endoscope cleaning/disinfecting apparatus comprising:
   a cleaning/disinfecting tank comprising a hollow portion,
      a perimeter fringe portion surrounding a perimeter of the hollow portion, and an arrangement portion where a cleaning/disinfecting target object is arranged, the arrangement portion being provided on a bottom surface of the hollow portion;
   a cover portion configured to automatically open and close freely relative to an opening of the cleaning/disinfecting tank;
   a facing portion provided on the cover portion and facing the perimeter fringe portion at a closed position where the cover portion covers the opening;
   an approach portion provided on an inner side with respect to the facing portion on the cover portion, the approach portion being fitted in the hollow portion at the closed position and, coming into contact or out of contact with the cleaning/disinfecting target object at the closed position;
   a central portion provided on an inner side with respect to the approach portion on the cover portion and covering the arrangement portion at the closed position;
   an acceleration sensor configured to detect a change pattern of acceleration of the cover portion when the cover portion moves from an open position to the closed position;
   an informing section configured to give a warning;
   a storage section in which a set pattern of the acceleration of the cover portion when the cover portion moves from the open position to the closed position is stored; and
   a control section configured to:
      perform automatic opening/closing control of the cover portion;
      compare the change pattern of the acceleration detected by the acceleration sensor and the set pattern; and
      when the change pattern of the acceleration is different from the set pattern:
         judge that the approach portion has come into contact with the cleaning disinfecting target object; and
         perform warning control of the informing section.

2. The endoscope cleaning/disinfecting apparatus according to claim 1, wherein the acceleration sensor is provided in the cover portion or a member moving between the open position and the closed position together with the cover portion.

3. The endoscope cleaning/disinfecting apparatus according to claim 1,
   wherein, if judging that the approach portion has come into contact with the cleaning/disinfecting target object, the control section is configured to perform automatic control to open the cover portion to an open position side.

4. The endoscope cleaning/disinfecting apparatus according to claim 1, further comprising:
   a watertight member provided on the inner side with respect to the approach portion on the cover portion, the watertight member being, at the closed position, pressed to the cleaning/disinfecting tank and deformed, to closely adhere to the cleaning/disinfecting tank,
   wherein the approach portion comes into contact with the cleaning/disinfecting target object when the cleaning/disinfecting target object protrudes to a side of the perimeter fringe portion surrounding the perimeter of the hollow portion with respect to the watertight member.

5. The endoscope cleaning/disinfecting apparatus according to claim 1, wherein the cover portion has a protruding portion protruding into the hollow portion at the closed position, and wherein the approach portion is provided at a position on the protruding portion which faces a side wall of the hollow portion at the closed position.

6. The endoscope cleaning/disinfecting apparatus according to claim 1, wherein the cover portion has a protruding portion protruding into the hollow portion at the closed position, and wherein the approach portion is provided at a position on the protruding portion which faces the bottom surface of the hollow portion at the closed position, wherein the approach portion comprises an elastic material.

7. The endoscope cleaning/disinfecting apparatus according to claim 1, wherein, when the approach portion is fitted into the hollow portion at the closed position, the distance is less than 2.5 mm.

8. The endoscope cleaning/disinfecting apparatus according to claim 1, wherein a shortest distance between the approach portion and the cleaning/disinfecting tank when the approach portion is fitted into the hollow portion at the closed position is less than 3.2 mm.

* * * * *